United States Patent

Hopmann et al.

(10) Patent No.: US 6,642,391 B2
(45) Date of Patent: Nov. 4, 2003

(54) AMYCOMYCIN, A PROCESS FOR ITS PRODUCTION AND ITS USE AS A PHARMACEUTICAL

(75) Inventors: Cordula Hopmann, Frankfurt am Main (DE); Michael Kurz, Hofheim (DE); Heinrich Decker, Bremtal (DE); Dominique Le Beller, Jaux (FR); Jozsef Aszodi, Pontault Combault (FR)

(73) Assignee: Aventis Pharma Deutschland GmbH, Frankfurt am Main (DE)

( * ) Notice: Subject to any disclaimer, the term of this patent is extended or adjusted under 35 U.S.C. 154(b) by 112 days.

(21) Appl. No.: 09/730,844

(22) Filed: Dec. 7, 2000

(65) Prior Publication Data

US 2001/0018450 A1 Aug. 30, 2001

(30) Foreign Application Priority Data

Dec. 8, 1999 (EP) .............................. 99124456

(51) Int. Cl.⁷ .................. C07D 207/44; A61K 31/4015
(52) U.S. Cl. ................... 548/540; 435/121; 514/423
(58) Field of Search .................. 548/540; 514/423; 435/121

(56) References Cited

FOREIGN PATENT DOCUMENTS

| EP | 0 816 539 A1 | 1/1998 |
|---|---|---|
| JP | XP-002138125 | 5/1992 |

Primary Examiner—Robert Gerstl
(74) Attorney, Agent, or Firm—Finnegan, Henderson, Farabow, Garrett and Dunner, L.L.P.

(57) ABSTRACT

A compound named Amycomycin of the formula:

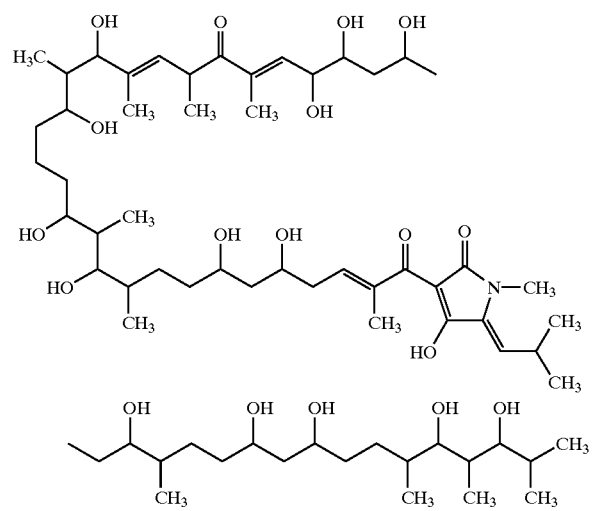

is described, as well as its pharmaceutically acceptable salts and derivatives, in all their stereoisomeric and tautomeric forms. The compound is obtained by growing the microorganism Amycolatopsis species ST101170 (DSM 12216) and is useful as a pharmaceutical, particularly as an antibiotic.

14 Claims, No Drawings

AMYCOMYCIN, A PROCESS FOR ITS PRODUCTION AND ITS USE AS A PHARMACEUTICAL

This invention relates to a compound named Amycomycin, which is obtainable by cultivation of the microorganism Amycolatopsis species ST101170 (DSM 12216), and to its pharmaceutically-acceptable salts and derivatives. The present invention further relates to a process for the production of Amycomycin, to the use of Amycomycin and its pharmaceutically-acceptable salts and derivatives as pharmaceuticals, in particular to their use as antibiotics, and to pharmaceutical compositions comprising Amycomycin or a pharmaceutically-acceptable salt or derivative thereof.

Methicillin resistant *Staphylococcus aureus* (MRSA) infections are known to be predominant in infectious conditions such as wounds and burns. Vancomycin and teicoplanin, which belong to the glycopeptide class, are the only two antibiotics clinically used for the treatment of MRSA infections. However, due to the recent emergence of vancomycin- and teicoplanin-resistant strains, these infections are reported to have become life-threatening and fatal. An intensive search for a structurally-different class of compounds active against these vancomycin- and teicoplanin-resistant strains has, therefore, been initiated. For instance, methylsulfomycin I, a cyclic thiopeptide, has been described earlier (EP-A-0818539 filed Jul. 11, 1996) as an antibiotic active against vancomycin- and teicoplanin-resistant strains.

It has now been found that a novel compound named Amycomycin has antibiotic activity. The present invention thus relates to a compound of the formula:

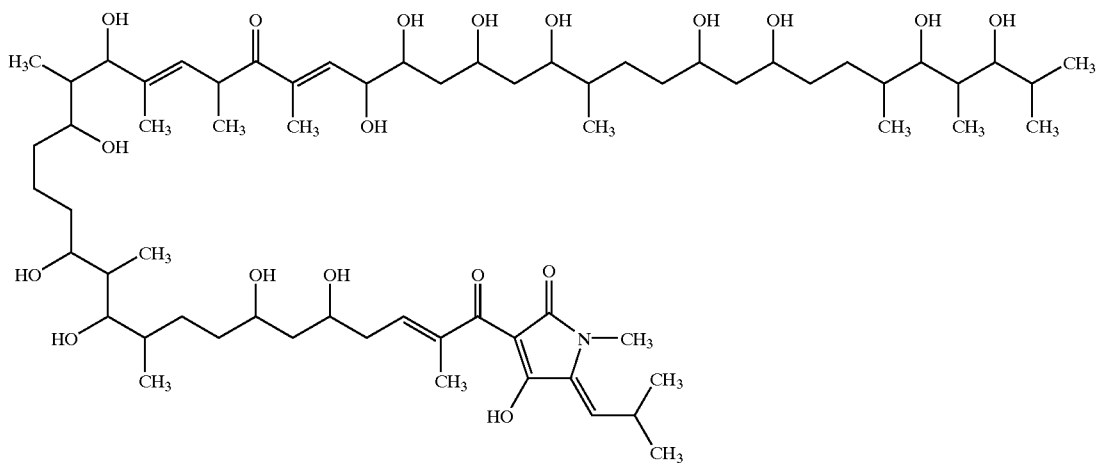

and to pharmaceutically-acceptable salts and derivatives thereof, such as esters, ethers and other obvious chemical equivalents, including all stereoisomeric forms and all tautomeric forms.

Amycomycin has a characteristic tetramic acid moiety with a highly oxygenated C45-side chain. It has the molecular formula $C_{65}H_{115}NO_{18}$ and is obtainable by cultivation of the microorganism Amycolatopsis species ST101170 (DSM 12216) under aerobic conditions in a nutrient medium containing sources of carbon and nitrogen, followed by isolation and purification in a customary manner. The microorganism ST101170 belongs to the order of Actinomycetales, genus Amycolatopsis, and was deposited on Jun. 4, 1998, with the German Collection of Microorganisms and Cell Cultures (DSMZ-Deutsche Sammlung von Mikroorganismen und Zelikulturen GmbH), Braunschweig, Deutschland and has been given the accession number DSM No. 12216.

The present invention further provides a process for the production of the compound named Amycomycin from Amycolatopsis species ST101170, its mutants and variants, under aerobic conditions in a nutrient medium containing one or more sources of carbon and one or more sources of nitrogen and optionally nutrient inorganic salts and/or trace elements, followed by isolation of the compound and purification in a customary manner.

Mutants and variants of the microorganism ST101170 may also be able to synthesize the compound according to the present invention. Such mutants may be produced in a known manner by physical means, for example, irradiation such as with ultraviolet- or X-rays, or with chemical mutagens, such as ethylmethylansulfonate (EMS), 2-hydroxy-4-methoxy-benzophenone (MOB) or N-methyl-N'-nitro-N-nitrosoguanidine (MNNG).

The screening for suitable mutants and variants that can produce the compound according to the invention can be confirmed by determination of the biological activity of the active compounds accumulated in the culture broth, for example, by testing the antibacterial action, in particular against vancomycin-resistant strains (see Table 2 below).

Preferred carbon sources suitable for aerobic fermentation are assimilable carbohydrate and sugar alcohols, such as glucose, lactose or D-mannitol as well as carbohydrate-containing natural products such as malt extract. Suitable sources of nitrogen are, for example, amino acids, peptides and proteins, including their degradation products such as peptones or tryptones, meat extract, ground seeds, for example, of maize, white beans, soya or the cotton plants, distillation residues from alcohol production, meat meal and yeast extracts, but also ammonium salts and nitrates. Suitable inorganic salts, which the nutrient solution may contain, are, for example, chlorides, carbonates, sulfates or phosphates of the alkaline metals or alkaline earth metals, ion, zinc, colbalt or manganese.

The formation of Amycomycin proceeds well, for example, in a nutrient medium comprising about 0.5 to 5% starch (soluble), preferably 1 to 2%, about 0.5 to 5% glucose, preferably 1 to 3%, about 0.5 to 5% glycerin, preferably 1 to 2%, about 0.1 to 0.5% corn steep liquor, preferably 0.2 to 0.3%, about 0.2 to 1% peptone, preferably 0.4 to 0.6%, about 0.1 to 0.5% yeast extract, preferably 0.2 to 0.4%, about 0.05 to 0.2% sodium chloride, preferably 0.1 to 0.2% and about 0.1 to 0.5% $CaCO_3$, preferably 0.2 to 0.3%. These amounts are based on the weight of the whole nutrient medium.

The growth of ST101170 is carried out aerobically, for example, in liquid medium with shaking or stirring in shake flasks or laboratory fermenters, optionally with the introduction or air or oxygen. Growth by fermentation can be carried out, for example, in sterile wide-necked bottles or round-bottomed flasks of various volumes, in glass fermenters or $V_2A$-steel tanks.

The growth of ST101170 may be carried out at temperatures between about 20° C. and about 35° C., preferably between about 25° C. and about 30° C. and pH between 4 and 10, preferably between 6 and 8. Under these conditions, the microorganism is grown in general over a period of 20 to 200 hours, preferably 24 to 150 hours.

Growth is advantageously carried out in several stages. Firstly, one or more pre-cultures may be prepared in a liquid nutrient medium. A main culture, the actual production medium, is then inoculated with the pre-culture in, for example, a volume ratio of 1:10. The pre-culture is obtained, for example, by inoculating a nutrient medium with sporified mycelium and allowing growth for about 20 to about 120 hours, preferably 24 to 90 hours. The sporified mycelium can be obtained, for example, by allowing the microorganism to grow for about 1 to about 40 days, preferably about 5 to about 12 days, on a solid or liquid nutrient medium such as yeast-malt agar or potato-dextrose agar.

The course of fermentation and the formation of Amycomycin can be monitored by methods known to the skilled person such as by measuring the biological activity of the culture broth in bioassays or by chromatographic methods such as thin-layer chromatography (TLC) or high-pressure liquid chromatography (HPLC).

The compound Amycomycin is present in the culture filtrate as well as in the mycelium. Usually, however, the highest amount is present in the mycelium. The compound can be isolated using known separation techniques. Thus, it can be recovered from the culture filtrate by, for example, filtration or centrifugation. The filtrate can be extracted with a water-immiscible solvent such as 1-butanol, ethyl acetate, chloroform, dichloromethane or the like, preferably 1-butanol or ethyl acetate.

The active material also can be recovered from mycelium by extraction with a water miscible solvent such as methanol, acetone, acetonitrile, n-propanol or iso-propanol, preferably methanol or acetone or a water immiscible solvent such as tert-butanol, ethyl acetate, chloroform, dichloromethanol or the like, preferably tert-butanol or ethyl acetate.

The extraction of the culture filtrate may be carried out within a wide pH range. It is preferable, however, for the extraction to be carried out in a neutral or weakly acidic medium, preferably at a pH of between 4 and 9. The organic extract may be concentrated in vacuum and dried to give the active crude material.

The isolation or purification of the compound Amycomycin may be carried out in a known manner taking into consideration the chemical, physical and biological characteristics of the natural compound.

One method of isolation of Amycomycin according to the invention is solution partition in a manner known to one skilled in the art.

Another method of purification of the Amycomycin is by chromatography on adsorption resins such as Diaion®  HP-20 (Mitsubishi Casei Corp., Tokyo), Amberlite® XAD 7 (Rohm and Haas, USA), Amberchrom® CG (Toso Haas, Philadelphia, USA), or similar resins. The separation can be carried out within a wide pH range. Preferably the pH range is 1 to 9, more preferably 2 to 8. Also suitable are numerous reverse phase supports, example $RP_8$ and $RP_{18}$, such as have been generally publicized in the context of high-pressure liquid chromatography (HPLC). A further possibility for purification of the compound according to the invention consists in the use of so-called normal-phase chromatographic supports such as silica gel, or $Al_2O_3$ (alumina) or others in a manner known to one skilled in the art. Many eluents are suitable for this, such as dichloromethane, chloroform, methanol, ethyl acetate, acetone, petroleum ether, or combinations thereof. The pH can be varied, for example, by addition of triethylamine.

An alternative isolation process of the compound Amycomycin is the use of molecular sieves such as Fractogel® TSK HW-40, Sephadex® LH-20, and others in a manner known per se. Moreover, it also is possible to recover the compound Amycomycin from the crude material by crystallization. Suitable therefor are, for example, organic solvents and their mixtures, anhydrous or with the addition of water.

An additional process for the isolation and purification of the compound according to the invention consists in the use of anion-exchangers, preferably in the pH range of from 7 to 10 and cation-exchangers, preferably in the pH range of from 3 to 7. Particularly suitable for this purpose is the use of buffer solutions to which amounts of the organic solvents have been added.

Additionally, counter-current chromatography using a biphasic eluent system made up of two or more solvents such as water, methanol, ethanol, butanol, isopropanol, acetone, dichloromethane, ethyl acetate, or petroleum ether, is a possible purification process.

The compound Amycomycin or chemical derivatives thereof can be converted to the corresponding pharmacologically-acceptable salts by methods known to one skilled in the art.

Pharmacologically-acceptable salts of compounds according to the invention are inorganic or organic salts such as are described in Remington's Pharmaceutical Sciences (17. Edition, page 1418 (1985)). Possible salts are alkali metal salts, ammonium salts, alkaline earth metal salts, salts with physiologically-acceptable amines and salts with inorganic or organic acids such as HCl, HBr, $H_2SO_4$, maleic acid and fumaric acid.

Obvious chemical equivalents of compounds according to the present invention are compounds that have a slight chemical difference but which have the same or similar activity or that, under mild conditions, can be converted to the compounds according to the present invention. Examples of obvious chemical equivalents are esters, ethers, amino derivatives, complexes or adducts of the compounds according to the invention.

Esters may be prepared, for example, by reacting Amycomycin with carboxylic acids in the presence of reagents such as dicyclohexylcarbodiimide (DCC), or by treating the compound with an acylating agent such as an acid chloride.

Ethers may be prepared, for example, from Amycomycin by reaction with alkylating agents under basic conditions.

Other methods for the preparation of esters and ethers are given in the literature, for example, in Advanced Organic Synthesis, $4^{th}$ Edition, J. March, John Wiley & Sons., 1992.

Chemical equivalents may be stable complexes with metal ions, e.g., transition metals like $La^{3+}$, $Sm^{3+}$, $Eu^{3+}$, $Gd^{3+}$, which are typical for tetramic acid derivatives and may be prepared by the methods given in the literature (K. Tanaka et. al., Chem. Pharm. Bull. 1979, 27, 1901. K. Matsuo, Chem. Pharm. Bull. 1980, 28, 2494).

The double bonds of the alkyl side chain may be reduced by the methods given in the literature, for example in P. N. Rylander, "Hydrogenation Methods", Academic Press, New York (1985), Chapter 2, or may be hydrohalogenated by methods described by H. O. House in "Modern Synthetic Reactions", W.A. Benjymin, Inc., New York (1972), pp 446-452. Hydroxylated derivatives may be produced by reaction of the double bonds with reagents like $OsO_4$ as described in the literature, e.g., in Chem. Rev. 80: 187 (1980).

Derivatives also may be formed by conversion of the double bonds into epoxides by oxidation, e.g., with MCPBA as described in Advanced Organic Synthesis, $4^{th}$ Edition, J. March, John Wiley & Sons., 1992.

The physical-chemical as well as the spectroscopic characteristics of the compound Amycomycin according to the invention are as follows:

| | |
|---|---|
| Appearance: | colorless solid, soluble in methanol, DMSO, pyridine |
| Molecular formula: | $C_{65}H_{115}NO_{18}$ |
| HPLC (High Pressure Liquid Chromatography): | |
| Column: | Purospher Star RP.18e (Merck), 55 × 4 mm, 3 μm |
| Eluent: | $CH_3CN/0,01\% H_3PO_4$ (85%) |
| Gradient: | Time (min)   % $CH_3CN$ |
| | 0.00   5.0 |
| | 3.00   95.0 |
| | 5.00   95.0 |
| | 6.00   5.0 |
| | 10.00   5.0 |
| Flow: | 2 ml/min |
| Temp.: | 40° C. |
| Detection: | 210 nm, 254, 280, 320, 380 |
| $t_R$: | 2.67 min |
| Molecular weight: | 1198.64 Da |
| HR-FAB-MS: | 1220.801187 $[M + Na]^+$ |
| $^1H$- and $^{13}C$-NMR: | see Table 1 |
| UV/VIS: | MeGH, $\lambda_{max}$ (log ε) = 229 nm (3.29), 281 (3.16) |

TABLE 1

Chemical shift of Amycomycin in MeOD at 300 K.

| | $^1H$ | $^{13}C$ |
|---|---|---|
| 1 | 0.86 | 14.76 |
| 2 | 0.97 | 20.83 |
| 3 | 1.89 | 31.20 |
| 4 | 3.41 | 82.20 |
| 5 | 1.70 | 39.55 |
| 6 | 0.77 | 13.63 |
| 7 | 3.54 | 80.19 |
| 8 | 1.65 | 36.32 |
| 9 | 0.86 | 12.71 |
| 10 | 1.43 | 31.20 |
| 11 | 1.44 | 36.46 |
| 12 | 3.75 | 71.98 |
| 13 | 1.62/1.54 | 44.79 |
| 14 | 3.74 | 72.22 |
| 15 | 1.58/1.37 | 36.46 |
| 16 | 1.63/1.14 | 29.27 |
| 17 | 1.51 | 40.69 |
| 18 | 0.90 | 15.70 |
| 19 | 3.70 | 72.90 |
| 27 | 1.51/1.46 | 42.12 |

TABLE 1-continued

Chemical shift of Amycomycin in MeOD at 300 K.

| | $^1H$ | $^{13}C$ |
|---|---|---|
| 28 | 4.07 | 66.31 |
| 29 | 1.52 | 42.12 |
| 30 | 3.80 | 72.54 |
| 31 | 4.33 | 73.26 |
| 32 | 6.62 | 142.18 |
| 33 | — | 138.47 |
| 34 | 1.83 | 12.75 |
| 35 | — | 206.04 |
| 36 | 4.21 | 41.00 |
| 37 | 1.14 | 17.77 |
| 38 | 5.36 | 128.37 |
| 39 | — | 138.72 |
| 40 | 1.69 | 12.75 |
| 41 | 3.98 | 80.54 |
| 42 | 1.64 | 41.25 |
| 43 | 0.88 | 8.02 |
| 44 | 3.59 | 73.88 |
| 45 | 1.49 | 36.46 |
| 46 | 1.62/1.32 | 23.50 |
| 47 | 1.55/1.32 | 33.34 |
| 48 | 3.80 | 75.09 |
| 49 | 1.74 | 42.71 |
| 50 | 0.77 | 11.92 |
| 51 | 3.41 | 77.87 |
| 52 | 1.61 | 36.46 |
| 53 | 0.86 | 12.75 |
| 54 | 1.55/1.32 | 31.37 |
| 55 | 1.61/1.44 | 36.46 |
| 56 | 3.77 | 71.83 |
| 57 | 1.67 | 44.53 |
| 58 | 3.92 | 71.12 |
| 59 | 2.30 | 37.54 |
| 60 | 5.84 (b) | ~131.7 (c) |
| 61 | — | (c) |
| 62 | 1.82 | 13.81 |
| 63 | — | (c) |
| 64 | — | (c) |
| 65 | 3.24 (b) | 27.91 |
| 66 | — | (c) |
| 67 | — | (c) |
| 68 | — | (c) |
| 69 | 5.50 (b) | ~119.3 (c) |
| 70 | 3.09 | 26.52 |
| 71 | 1.10 | 24.31 |
| 72 | 1.10 | 24.31 |

(b) Broad signals
(c) These signals are not visible. C60 und C69 could only be assigned with the HMQC-spectrum.

Amycomycin has extraordinary antibacterial activity, particularly against gram-positive bacteria such as, for example, Staphylo- and Enterococci. Minimum inhibitory concentrations of Amycomycin against a wide range of bacteria are given in Table 2 below. Lately, these strains have proven increasingly to be problem strains, i.e., those microorganisms that have become resistant to existing antibiotics. The superiority of the present compound in relation to other antibiotics is shown, for example, in the inhibition of vancomycin- and teicoplanin-resistant strains such as, for example, *E. faecalis, E. faecium* or *E. gallinarium*.

TABLE 2

Minimum Inhibition Concentration (mg/L) (micro-dilutions test)

| | CODE | | Amycomycin | Vancomycin |
|---|---|---|---|---|
| Gram-positive Strain | | | | |
| S.aureus | 011HT3 | oxa S ery S | 0.08 | 0.3 |
| S.aureus | 011HT18 | ATCC 13709 Smith | 0.08 | 0.3 |
| S.epidermidis | 012GO20 | oxa S ery S tet R | 0.3 | 0.6 |
| S.aureus | 011HT1 | nov R | <=0.04 | 0.08 |
| S.aureus | 011DU5 | nov R tet R | 0.08 | 0.15 |
| S.aureus | 011CB20 | oxa R ery Rc tet R | 0.08 | 0.15 |
| S.aureus | 011GO71 | ofl S oxa R ery S tet R | 0.15 | 0.6 |
| S.aureus | 011GO64 | ofl R oxa R ery Rc tet R | 0.3 | 1.2 |
| S.epidermidis | 012GO42 | oxa R | 0.3 | 1.2 |
| Staph.coag.negative | 012HT5 | ofl R oxa R tet R | 0.15 | 0.6 |
| S.aureus | 011GR91 | pri R oxa R ery R nov R | 1.2 | 1.2 |
| S.pyogenes | O2A1SJ1 | van S ery Rc | 0.3 | 0.15 |
| S.pyogenes | O2A1UC1 | van S ery S | 0.6 | 0.15 |
| S.pyogenes | O2A1FI6 | ery R | 0.6 | 0.08 |
| Strepto gr.G | O2G0CB2 | tet R rif R nov R | 0.6 | 0.15 |
| S.pneumoniae | 030BI2 | ery R | 0.15 | 0.15 |
| S.milleri | O2milGR12 | ery S van S | 1.2 | 0.3 |
| S.mitis | O2mitGR16 | ery Ri van S | 1.2 | 0.3 |
| E.faecium | O2D3AP9 | nov S van R ery S tei R | 0.6 | >40 |
| E.faecium | O2D3HT12 | tei R van R ery R tet R | 0.6 | >40 |
| E.faecium | O2D3IP2 | tei R van R ery R tet R | ND | >40 |
| E.faecium | O2D3HM3 | nov S van A ery R tei R | 1.2 | >40 |
| E.gallinarium | O2D0HM8 | van C tet R ery S | 1.2 | >40 |
| E.faecalis | O2D2HM9 | nov R van B ery R tei S | 2.5 | >40 |
| E.faecalis | O2D2UC5 | ATCC 29212 nov R | 2.5 | 2.5 |
| E.faecalis | O2D2DU18 | tet R nov R | 1.2 | 0.3 |
| E.faecalis | O2D2HT10 | nov R van S tet R | 1.2 | 0.6 |
| Gram-negative Strain | | | | |
| E.coli | DB10 250IP5 | ery S fuc S nov S | ND | >40 |
| P.aeruginosa | 1771 391HT2 | | >40 | >40 |
| P.aeruginosa | 1771m 391HT3 | mutant perméable | >40 | >40 |

Amycomycin and its pharmaceutically-acceptable salts and derivatives can be administered to animals, preferable to mammals, and in particular to humans as pharmaceuticals on their own, in mixtures with one another, and in the form of pharmaceutical compositions that permit parenteral or other modes of administration. Accordingly, the present invention also relates to Amycomycin and its pharmaceutically-acceptable salts and derivatives for use as pharmaceuticals and to the use of Amycomycin and its pharmaceutically-acceptable salts and derivatives for the production of medicaments having antibacterial activity. The present invention further relates to pharmaceutical compositions which contain an effective amount of Amycomycin and/or one or more pharmaceutically-acceptable salts and/or derivatives thereof, together with a pharmaceutically-acceptable carrier.

Amycomycin can be administered enterally (oral route), parenterally (intravenously or intramuscularly) rectally or locally (topically). Pharmaceutical compositions that contain Amycomycin or a pharmaceutically-acceptable salt or derivative thereof with other pharmaceutically-active substances can be prepared by mixing the active compounds with one or more pharmacologically-tolerated auxiliaries and/or excipients, and converting the mixture into a suitable pharmaceutical form for administration, such as, solutions, powders (tablets, capsules including microcapsules), ointments (creams or gels), liposome preparations, lipid complexes, coloidal dispersions, or suppositories.

Possible auxiliaries and/or excipients for formulations of this type are the pharmaceutically-customary liquid or solid fillers and extenders, solvents, emulsifiers, lubricants, flavor corrigents, colorants and/or buffer substances.

As is customary, the pharmaceutical formulation and the method of administration, as well as the dosage range, that are suitable in a specific case depend on the species to be treated and on the state of the respective condition or disease, and can be optimized using methods known in the art. As an example, a dose of 0.001–10 mg, preferably 0.1–5 mg, more preferably 1.0 mg for a body weight of approx. 75 kg may be suitable. The dose should at least be sufficient to produce the desired effect.

The following are illustrative examples of the present invention but do not limit the scope thereof:

EXAMPLE 1

Preparation of Seed Material 100 ml of nutrient solution (4 g/l yeast extract, 15 g/l soluble starch, 1 g/l $K_2HPO_4$, 0.5 g/l $MgSO_4 \times 7$ $H_2O$ filled with water to 1000 ml, pH 7.0 before sterilization) in a sterile 300 ml Erlenmeyer flask were inoculated with the strain Amycolatopsis species ST101170 (DSM 12216) and incubated for 5 days at 28° C. and at 180 rpm on a rotary shaker. 1.5 ml of this culture was subsequently diluted with 1.5 ml of 99% glycerin and stored at −20° C.

EXAMPLE 2

Preparation of Culture or Pre-culture of Amycolatopsis Species ST101170 (DSM 12216) in Erlenmeyer Flasks A sterile Erlenmeyer flask containing 100 ml of the following nutrient medium: 10 g/l starch solution, 10 g/l glucose, 10 g/l glycerin 99%, 2.5 g/l corn steep fluid or liquor, 5 g/l peptone, 2 g/l yeast extract, 1 g/l NaCl, and 3 g/l $CaCO_3$, was inoculated with a loopful of grown culture (same nutrient solution, but with 2% agar) or with 1 ml of a glycerin culture (see Example 1) and incubated on a shaker at 180 rpm and at 28° C. Maximum production of the compound Amycomycin was reached after 72 hours.

A 72 hour old submersed culture (produced according to the described process for the shake culture, Example 1, but with the following medium: 15 g/l glucose, 15 g/l soyameal, 3 g/l $CaCO_3$ and 5 g/l NaCl, pH 7.5) was sufficient for the inoculation of 10 and 200 L fermenters with an inoculation amount of 10%.

EXAMPLE 3

Production of the Compound Amycomycin

A 200 L fermenter was run with the following parameters:

| Nutrient medium: | 10 g/L starch |
| --- | --- |
| | 10 g/L glucose |
| | 10 g/L glycerin 99% |
| | 2.5 g/L cornsteep liquor |
| | 5 g/L peptone |
| | 2 g/L yeast extract |
| | 7 g/L NaCl |
| | 3 g/L $CaCO_3$ |
| | pH 7.2 (before sterilization) |
| Inoculum: | 10% fermenter volume |
| Incubation time: | 60 to 80 hours |
| Incubation temperature: | 28° C. |
| Agitation: | 50 rpm |
| Aeration: | 150 L/min |

By addition of 1 to 2 ml of an ethanolic polyol solution it was possible to limit foam formation. The production maximum was reached after 69 hours.

EXAMPLE 4

Isolation of the Compound Amycomycin

200 L of the culture solution obtained from Example 3 was centrifuged and the mycelium was exhaustively extracted with methanol. The methanol extract was concentrated to a ratio of approximately 1:10 to obtain a colorless precipitate, which was filtered off. This procedure was repeated until the substance Amycomycin could no longer be detected in the filtrate by reverse phase HPLC. The residue was freeze-dried and subsequently purified by HPLC:

1. Column: ®Fractogel TSK-HW 40 (4 L, 500×100 mm)
Eluent: MeOH
Flow Rate: 20 ml/min
Detection: 204 and 236 nm.

The fractions enriched with Amycomycin eluted after 125 minutes. Fractions were pooled based on reverse phase HPLC (conditions mentioned above). The active pooled fractions with the desired compound were concentrated under vacuum and freeze-dried.

2. Column: Silica Gel 60 (Merck); Erimatech (300×20 mm, 100 ml)

| Eluent: | A) $CH_2Cl_2$ | B) $CH_2Cl_2$:MeOH 9:1 | C) MeOH. |
| --- | --- | --- | --- |
| Gradient: | min | % A | % B | % C |
| | 0 | 100 | 0 | 0 |
| | 15 | 100 | 0 | 0 |
| | 35 | 0 | 100 | 0 |
| | 45 | 0 | 100 | 0 |
| | 65 | 0 | 0 | 100 |
| Flow Rate: | 25 ml/min | | | |
| Detection: | 236 and 288 nm | | | |

The active compound Amycomycin eluted after 42 minutes. Fractions were pooled based on reverse phase HPLC (conditions mentioned above). The active pooled fractions with the desired compound were concentrated in vacuum and freeze-dried.

3. Column: ® Fractogel TSK-HW 40 (1 L, 500×50 mm)
Eluent: MeOH
Flow Rate: 5 ml/min
Detection: 204 and 236 nm The active component Amycomycin eluted after 112 minutes.

From 200 L fermentation broth, 110 mg of Amycomycin was recovered according to the above process.

We claim:

1. A compound of the formula:

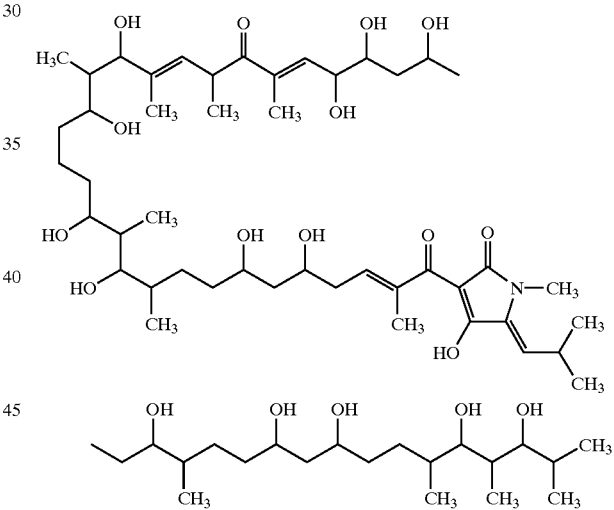

including tautomeric forms and pharmaceutically-acceptable salts of said compound.

2. A compound of the molecular formula $C_{65}H_{115}NO_{18}$, including tautomeric forms and pharmaceutically-acceptable salts of said compound, wherein said compound is obtained by growing the microorganism Amycolatopsis species ST101170 (DSM 12216) under aerobic conditions in a nutrient medium containing sources of carbon and nitrogen, followed by isolation and purification.

3. A process for the production of the compound of claim 1, comprising the steps of growing the microorganism Amycolatopsis species ST101170 (DSM 12216) under aerobic conditions in a nutrient medium containing sources of carbon and nitrogen and isolating and purifying the compound.

4. The process according to claim 3, further comprising converting the compound into a pharmacologically-tolerable salt, ester, ether or other chemical equivalent.

5. A pharmaceutical composition, comprising the compound according to claim 1 and a pharmaceutically-acceptable carrier.

6. A process for the production of the compound of claim 2, comprising the steps of growing the microorganism Amycolatopsis species ST101170 (DSM 12216) under aerobic conditions in a nutrient medium containing sources of carbon and nitrogen and isolating and purifying the compound.

7. The process according to claim 6, further comprising converting the compound into a pharmacologically-tolerable salt, ester, ether or other chemical equivalent.

8. A pharmaceutical composition, comprising the compound according to claim 2 and a pharmaceutically-acceptable carrier.

9. A method for inhibiting the growth of bacteria, comprising exposing said bacteria to at least a minimum inhibitory concentration of the compound according to claim 1.

10. The method according to claim 9, wherein said bacteria are gram-positive bacteria.

11. The method according to claim 9, wherein said bacteria are selected from the group consisting of *Staphylococcus aureus, Staphylococcus epidermis, Streptococcus pyogenes, Streptococcus pneumoniae, Enterococcus faecalis, Enterococcus faecium*, and *Enterococcus gallinarium*.

12. A method for inhibiting the growth of bacteria, comprising exposing said bacteria to at least a minimum inhibitory concentration of the compound according to claim 2.

13. The method according to claim 12, wherein said bacteria are gram-positive bacteria.

14. The method according to claim 12, wherein said bacteria are selected from the group consisting of *Staphylococcus aureus, Staphylococcus epidermis, Streptococcus pyogenes, Streptococcus pneumoniae, Enterococcus faecalis, Enterococcus faecium*, and *Enterococcus gallinarium*.

* * * * *

UNITED STATES PATENT AND TRADEMARK OFFICE
CERTIFICATE OF CORRECTION

PATENT NO. : 6,642,391 B2
DATED : November 4, 2003
INVENTOR(S) : Cordula Hopmann et al.

It is certified that error appears in the above-identified patent and that said Letters Patent is hereby corrected as shown below:

Column 10,
Lines 66-67, "pharmacologically-tolerable salt, ester, ether or other chemical equivalent." should read -- pharmaceutically-acceptable salt. --.

Column 11,
Lines 11-12, "pharmacologically-tolerable salt, ester, ether or other chemical equivalent." should read -- pharmaceutically-acceptable salt. --.

Signed and Sealed this

Tenth Day of August, 2004

JON W. DUDAS
*Acting Director of the United States Patent and Trademark Office*